US012654144B2

(12) United States Patent
Linder et al.

(10) Patent No.: US 12,654,144 B2
(45) Date of Patent: Jun. 16, 2026

(54) PROCESS FOR THE PREPARATION OF HIGH WATER AFFINITY TYPE PRODUCTS WITH CONTROLLED HUMIDITY

(71) Applicant: Hoffmann-La Roche Inc., Little Falls, NJ (US)

(72) Inventors: David Linder, Basel (CH); Kurt Puentener, Ueken (CH); Martin Olbrich, Lorrach (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 930 days.

(21) Appl. No.: 17/559,041

(22) Filed: Dec. 22, 2021

(65) Prior Publication Data

US 2022/0331763 A1 Oct. 20, 2022

Related U.S. Application Data

(63) Continuation of application No. PCT/EP2020/068318, filed on Jun. 30, 2020.

(30) Foreign Application Priority Data

Jul. 2, 2019 (EP) .................................... 19183894

(51) Int. Cl.

| | |
|---|---|
| ***B01D 1/18*** | (2006.01) |
| ***B01J 2/04*** | (2006.01) |
| ***C07H 21/02*** | (2006.01) |
| ***C07H 21/04*** | (2006.01) |

(52) U.S. Cl.

CPC ..................................... *B01J 2/04* (2013.01); *B01D 1/18* (2013.01); *C07H 21/02* (2013.01); *C07H 21/04* (2013.01)

(58) Field of Classification Search

CPC ........................................................ B01D 1/18

See application file for complete search history.

(56) References Cited

U.S. PATENT DOCUMENTS

| | | | | |
|---|---|---|---|---|
| 5,928,469 A * | 7/1999 | Franks | C12N 11/02 | 159/48.1 |
| 6,071,428 A * | 6/2000 | Franks | A61K 47/26 | 124/58 |
| 6,426,210 B1 * | 7/2002 | Franks | C12N 9/96 | 424/93.4 |
| 11,021,503 B2 * | 6/2021 | Breitler | A61K 47/549 | |
| 11,339,187 B2 * | 5/2022 | Breitler | C07H 15/08 | |

(Continued)

FOREIGN PATENT DOCUMENTS

| | | |
|---|---|---|
| CN | 102228440 A | 11/2011 |
| WO | 97/35562 | 10/1997 |

(Continued)

OTHER PUBLICATIONS

"Plasmids are autonomous circular oligonucleotides", BioSythesis, Feb. 20, 2015, https://www.biosyn.com/tew/plasmids-are-autonomous-circular-oligonucleotides.aspx.*

(Continued)

*Primary Examiner* — Jonathan Luke Pilcher

(74) *Attorney, Agent, or Firm* — Hoffmann-La Roche Inc.

(57) ABSTRACT

The invention relates to a new process for the preparation of high water affinity type products with controlled humidity via spray drying in a suitable spray drying equipment applying specific spray drying parameters.

12 Claims, 1 Drawing Sheet

Specification includes a Sequence Listing.

(56) References Cited

U.S. PATENT DOCUMENTS

| | | | | |
|---|---|---|---|---|
| 2003/0040462 | A1* | 2/2003 | Franks | A61K 35/12 435/2 |
| 2003/0124193 | A1* | 7/2003 | Snyder | A61P 31/00 264/12 |
| 2004/0052840 | A1* | 3/2004 | Kubota | A61K 31/7105 424/468 |
| 2004/0092470 | A1* | 5/2004 | Leonard | A61K 9/141 424/46 |
| 2004/0197413 | A1* | 10/2004 | Sheu | A61K 9/1694 424/489 |
| 2005/0106553 | A1* | 5/2005 | Franks | C07K 17/02 435/2 |
| 2005/0209122 | A1 | 9/2005 | Jorgensen et al. | |
| 2008/0108554 | A1 | 5/2008 | Jackson et al. | |
| 2009/0258933 | A1* | 10/2009 | Kubota | A61K 9/0019 514/44 R |
| 2010/0111984 | A1* | 5/2010 | D'Souza | A61K 9/5169 435/375 |
| 2011/0028535 | A1* | 2/2011 | Kubota | A61K 48/0008 514/44 A |
| 2011/0243988 | A1* | 10/2011 | Ohtake | A61P 37/02 424/234.1 |
| 2017/0042817 | A1 | 2/2017 | Teo et al. | |
| 2021/0388359 | A1* | 12/2021 | Appeldorff Larsen | C12Q 1/68 |

FOREIGN PATENT DOCUMENTS

| | | | |
|---|---|---|---|
| WO | 2003/080028 | | 10/2003 |
| WO | 2009/090189 | | 7/2009 |
| WO | 2010/072621 | | 7/2010 |
| WO | 2011/154014 | A1 | 12/2011 |
| WO | 2015/051283 | A1 | 4/2015 |
| WO | 2018/069777 | | 4/2018 |
| WO | 2018/215391 | A1 | 11/2018 |

OTHER PUBLICATIONS

"International Prelimiary Report on Patentability—PCT/EP2020/068318" (Report Issuance Date: Dec. 28, 2021; Chapter I), :pp. 1-8 (Jan. 13, 2022).

"International Search Report—PCT/EP2020/068318" (w/Written Opinion), :pp. 1-12 (Oct. 26, 2020).

Santos et al., "Spray drying: an overview" Biomaterials-Physics and Chemistry-New Edition Chapter 2:pp. 9-35 (2018).

* cited by examiner

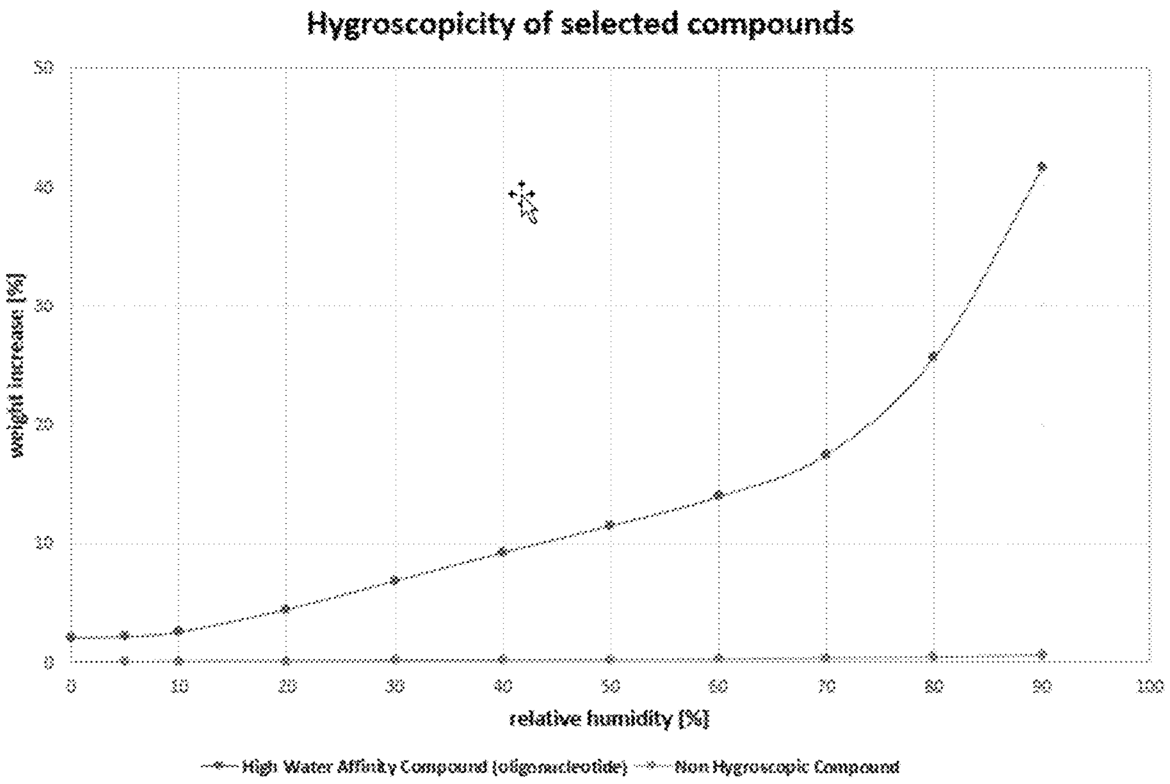
Hygroscopicity of selected compounds
weight increase [%]
50
40
30
20
10
0
0
10
20
30
40
50
60
70
80
90
100
relative humidity [%]
High Water Affinity Compound (oligonucleotide)
Non Hygroscopic Compound

```
                              SEQUENCE LISTING

<160> NUMBER OF SEQ ID NOS: 3

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

cagcgtaaag agagg                                                        15


<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

tggcaagcat cctgta                                                       16


<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

cacctattta acatcagac                                                    19
```

PROCESS FOR THE PREPARATION OF HIGH WATER AFFINITY TYPE PRODUCTS WITH CONTROLLED HUMIDITY

CROSS REFERENCE TO RELATED APPLICATIONS

This application is a continuation of International Application No. PCT/EP2020/068318, filed Jun. 30, 2020, which claims priority to European Application No. 19183894.5, filed Jul. 2, 2019, which are incorporated herein by reference in its entirety.

SEQUENCE LISTING

This application contains a Sequence Listing, which has been submitted electronically in ASCII format and is hereby incorporated by reference in its entirety. Said ASCII copy, created on Jun. 7, 2022, is named P35611-US-SL.txt and is 1,079 bytes in size.

The invention comprises a process for the preparation of high water affinity type products with controlled humidity via spray drying in a suitable spray drying equipment applying the following spray drying parameters:

| | |
|---|---|
| Inlet $N_2$ temperature (° C.) | 150 to 300 |
| Outlet $N_2$ temperature (° C.) | 50 to 150 |

thereby controlling the water content of the spray dried high water affinity type product in a range of 1 w/w to 20% w/w.

High water affinity type products such as oligonucleotides are for the purpose of obtaining the product in solid form often lyophilized. Due to its high hygroscopicity the lyophilized powders of the high water affinity type products tend to be electrostatically charged, not free flowing and therefore very difficult to manage. In order to achieve a certain humidity and a manageable form of the powder the lyophilized powders as a rule undergo an extra conditioning procedure wherein the powder is exposed to water vapor in in a climate chamber at a certain temperature and humidity (cf. WO 2018/215391; page 69, line 5).

This extra step is time and resources consuming and disadvantageous for a larger scale manufacture of such products.

Object of the present invention therefore was to find a process which avoids this extra conditioning step and which allows to produce high water affinity type products with controlled humidity.

It was found that the object of the invention could be reached with the process for the preparation of high water affinity type products with controlled humidity, which is characterized in that an aqueous solution of the high water affinity type product is spray dried in a suitable spray drying equipment applying the following spray drying parameters:

| | |
|---|---|
| Inlet $N_2$ temperature (° C.) | 150 to 300 |
| Outlet $N_2$ temperature (° C.) | 50 to 150 |

thereby controlling the water content of the spray dried high water affinity type product in a range of 1 w/w to 20% w/w.

The following definitions are set forth to illustrate and define the meaning and scope of the various terms used to describe the invention herein.

The term high water affinity type products means products which due to its molecule structure show high polarity and therefore a high affinity to water (and thus display a very high hygroscopicity). Examples of such products are peptides or oligonucleotides.

In a preferred embodiment the term high water affinity type product stands for an oligonucleotide.

FIG. 1 illustrates the characteristic of a high water affinity oligonucleotide to absorb water thereby gaining weight in relation to the relative humidity compared to a non-hygroscopic compound.

The term oligonucleotide as used herein is defined as it is generally understood by the skilled person as a molecule comprising two or more covalently linked nucleotides. For use as a therapeutically valuable oligonucleotide, oligonucleotides are typically synthesized as 10 to 40 nucleotides, preferably 10 to 25 nucleotides in length.

The oligonucleotides may consist of optionally modified DNA, RNA or LNA nucleoside monomers or combinations thereof.

The LNA nucleoside monomers are modified nucleosides which comprise a linker group (referred to as a biradicle or a bridge) between C2' and C4' of the ribose sugar ring of a nucleotide. These nucleosides are also termed bridged nucleic acid or bicyclic nucleic acid (BNA) in the literature.

Optionally modified as used herein refers to nucleosides modified as compared to the equivalent DNA, RNA or LNA nucleoside by the introduction of one or more modifications of the sugar moiety or the nucleo base moiety. In a preferred embodiment the modified nucleoside comprises a modified sugar moiety, and may for example comprise one or more 2' substituted nucleosides and/or one or more LNA nucleosides. The term modified nucleoside may also be used herein interchangeably with the term "nucleoside analogue" or modified "units" or modified "monomers".

The DNA, RNA or LNA nucleosides are as a rule linked by a phosphodiester (P=O) and/or a phosphorothioate (P=S) internucleoside linkage which covalently couples two nucleosides together.

Accordingly, in some oligonucleotides all internucleoside linkages may consist of a phosphodiester (P=O), in other oligonucleotides all internucleoside linkages may consist of a phosphorothioate (P=S) or in still other oligonucleotides the sequence of internucleoside linkages vary and comprise both phosphodiester (P=O) and phosphorothioate (P=S) internucleoside.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are described with capital letters A, T, G and $^{Me}$C (5-methyl cytosine) for LNA nucleoside and with small letters a, t, g, c and $^{Me}$C for DNA nucleosides. Modified nucleobases include but are not limited to nucleobases carrying protecting groups such as tert.butylphenoxyacetyl, phenoxyacetyl, benzoyl, acetyl, isobutyryl or dimethylformamidino (see Wikipedia, Phosphoramidit-Synthese, https://de.wikipedia.org/wild/Phosphoramidit-Synthese of Mar. 24, 2016).

Preferably the oligonucleotide consists of optionally modified DNA, RNA or LNA nucleoside monomers or combinations thereof and is 10 to 40, preferably 10 to 25 nucleotides in length.

The oligonucleotide can be 5' amino modified which signifies that an amino linker is attached to the 5' terminal group of the oligonucleotide. The linker preferably is an aliphatic alkyl group of 2 to 12 carbon atoms or an ethylene glycol linker containing 1 to 10 ethylene glycol units.

The preferred 5' amino-modifier is selected from an optionally amino group protected amino $C_{2-12}$-alkyl linker or an amino ethylene glycol linker containing 1 to 10 ethylene glycol units.

Suitable amino protecting groups for the 5' amino modified oligonucleotide are trifluoroacetyl (TFA) or monomethoxytrityl (MMT).

As a rule the amino linker is introduced via a commercially available amino linker phosphoroamidite such as for instance via the TFA- or MMT-$C_6$-linker phosphoroamidites e.g. from Sigma Aldrich or via the 5' amino modifier TEG (triethyleneglycol) CE phosphoroamidite from Glen Research.

The principles of the oligonucleotide synthesis are well known in the art (see e.g. Oligonucleotide synthesis; Wikipedia, the free encyclopedia; https://en.wikipedia.org/wiki/Oligonucleotide synthesis, of Mar. 15, 2016).

Larger scale oligonucleotide synthesis nowadays is carried automatically using computer controlled synthesizers.

As a rule, oligonucleotide synthesis is a solid-phase synthesis, wherein the oligonucleotide being assembled is covalently bound, via its 3'-terminal hydroxy group, to a solid support material and remains attached to it over the entire course of the chain assembly. Suitable supports are the commercial available macroporous polystyrene supports like the Primer support 5G from GE Healthcare or the NittoPhase®HL support from Kinovate.

The oligonucleotide synthesis in principle is a stepwise addition of nucleotide residues to the 5'-terminus of the growing chain until the desired sequence is assembled.

As a rule, each addition is referred to as a synthetic cycle and in principle consists of the chemical reactions

- a1) de-blocking the protected hydroxyl group on the solid support,
- a2) coupling the first nucleoside as activated phosphoramidite with the free hydroxyl group on the solid support,
- a3) oxidizing or sulfurizing the respective P-linked nucleoside to form the respective phosphodiester (P═O) or the respective phosphorothioate (P═S);
- a4) optionally, capping any unreacted hydroxyl groups on the solid support;
- a5) de-blocking the 5' hydroxyl group of the first nucleoside attached to the solid support;
- a6) coupling the second nucleoside as activated phosphoramidite to form the respective P-linked dimer;
- a7) oxidizing or sulfurizing the respective P-linked dinucleoside to form the respective phosphodiester (P═O) or the respective phosphorothioate (P═S);
- a8) optionally, capping any unreacted 5' hydroxyl groups;
- a9) repeating the previous steps a5 to a8 until the desired sequence is assembled.

The subsequent cleavage from the resin can be performed with concentrated aqueous ammonia. The protecting groups on the phosphate and the nucleotide base are also removed within this cleavage procedure.

In a further embodiment the oligonucleotide may comprise cell targeting moieties for targeting the oligonucleotide to a given receptor, such as for instance the asyalglycoprotein receptor (c.f. X. Huang et al, Bioconjugate. Chem. 2017, 28, 283-295)

In a preferred embodiment the cell targeting moiety comprises 1 to 3 N-acetyl galactosamine (GalNAc) ligands.

Typical GalNAc comprising cell targeting moieties can be selected from:

I

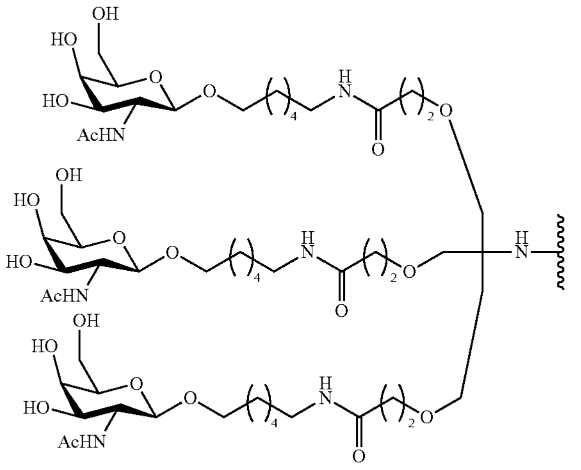

II

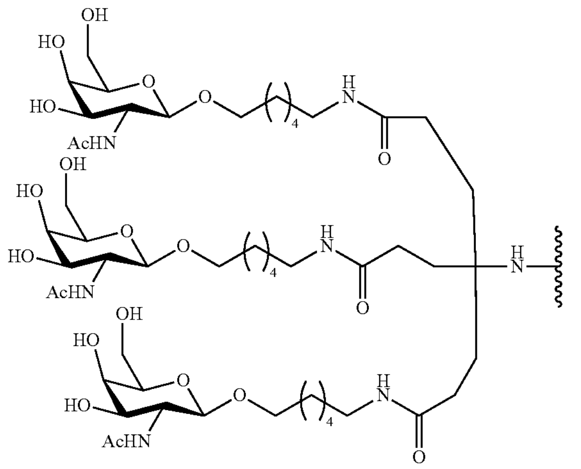

III

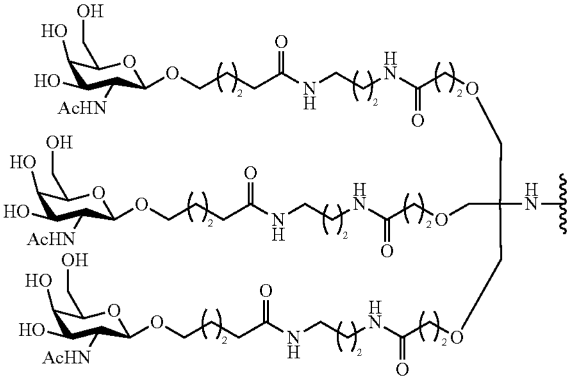

-continued

IV

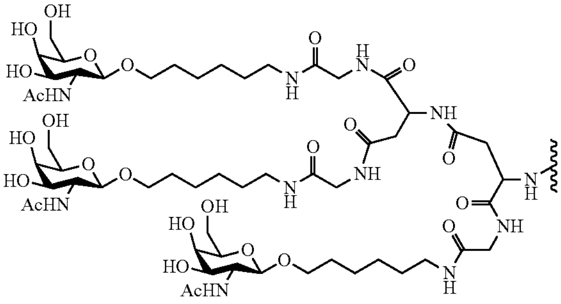

or from moieties of the formula

V

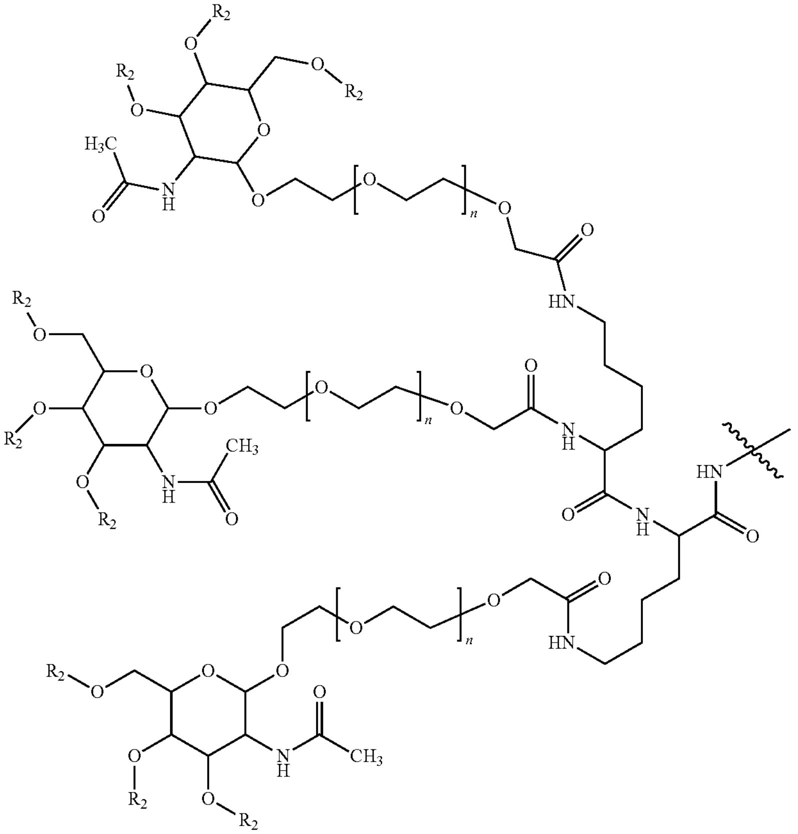

wherein $R^2$ is hydrogen or a hydroxy protecting group and n is an integer from 0 to 10, preferably an integer from 0 to 5, more preferably from 1 to 3, but most preferred is 2, enantiomers and/or a stereoisomers thereof.

Suitable hydroxy protecting groups are acyl, particularly the $C_{1-12}$-alkylcarbonyl group, more particularly the $C_{1-6}$-alkylcarbonyl group which is optionally substituted by $C_{1-6}$-alkyl or phenyl. More preferred is acetyl, pivaloyl or benzoyl, whereby acetyl is the most preferred hydroxy protecting group.

In a more preferred embodiment the GalNAc comprising cell targeting moieties can be selected from the moiety of formula V.

In a further preferred embodiment the oligonucleotide is a GalNAc oligonucleotide conjugate comprising a 5' amino modified oligonucleotide as described above.

The purification of the high water affinity type products follows methods which as a rule are known to the skilled in the art for the type of products.

Typically the purification comprises steps of chromatography, of concentration and of isolation, whereas the chromatography and concentration steps can be applied repeatedly.

For the oligonucleotides as preferred high water affinity type products suitable purification procedures comprise the sequence of the steps a) chromatography
b) concentration
c) isolation or preferably, d) anion exchange chromatography or reversed phase chromatography
e) tangential flow filtration
f) lyophilization The term chromatography comprises the methods anion exchange chromatography or reversed phase chromatography and combinations thereof.

The anion-exchange chromatography is based on the competitive interaction of charged ions of the sample solution with the buffer medium employed. It can be carried out with conventional, commercially available anion-exchange resins, preferably those with trimethylammonium-functionalization. These phase materials can be obtained for example from GE Healthcare, Tosoh Bioscience, Bio-Rad or Merck.

Particular good results have been achieved with the anion-exchange resin TSKgel Super Q-5PW (QAE), available from Tosoh Bioscience.

The reversed-phase chromatography can be carried out with traditional, commercially available phase materials such as a modified silica gel sorbents as stationary phase and suitable organic solvents such as acetonitrile and, if applicable, a buffer. Suitable modified silica gel type phase materials can be selected from Kromasil™C18, Kromasil™C8, YMC Triart C18 and YMC Triart C8. Particular good results have been achieved with the Triart Prep C8-S from YMC.

The term concentration comprises the methods tangential flow filtration or evaporation and combinations thereof.

In the tangential flow filtration or cross flow filtration the feed is passed across the filter membrane (tangentially) at positive pressure relative to the permeate side. A proportion of the material which is smaller than the membrane pore size passes through the membrane as permeate or filtrate; everything else is retained on the feed side of the membrane as retentate. The principles of tangential flow filtration is also used in nanofiltration, ultrafiltration, diafiltration and microfiltration processes. Suitable membranes are commercially available, for instance from Merck Millipore under the trade name Pellicon™. Suitable membranes have a molecular weight cut-off (MWCO) of ≤3 kDA. The Merck Millipore Pellicon 2 and 3 membranes with an MWCO of 1 kDA or 3 kDA respectively are preferred.

As outlined above the process for the preparation of high water affinity type products with controlled humidity, is characterized in that an aqueous solution of the high water affinity type product is spray dried in a suitable spray drying equipment applying the following spray drying parameters:

| | |
|---|---|
| Inlet $N_2$ temperature (° C.) | 150 to 300 |
| Outlet $N_2$ temperature (° C.) | 50 to 150 |

thereby controlling the water content of the spray dried high water affinity type product in a range of 1 w/w to 20% w/w.

In a preferred embodiment the spray drying parameters are:

| | |
|---|---|
| High water affinity type product concentration in the feed solution (% w/w) | 1 to 50 |
| Inlet $N_2$ temperature (° C.) | 180 to 220 |
| Outlet $N_2$ temperature (° C.) | 70 to 100 |

In a more preferred embodiment the spray drying parameters are:

| | |
|---|---|
| High water affinity type product concentration in the feed solution (% w/w) | 5 to 25 |
| Inlet $N_2$ temperature (° C.) | 180 to 220 |
| Outlet $N_2$ temperature (° C.) | 70 to 100 |

The process parameters as a rule depend on the spray drying equipment applied.

However, the ratio Gas rate drying/Feed rate and the ratio Gas rate nozzle/Feed rate ratio are dimension-less parameters independent from the size of the drying chamber and the type of atomizer.

Typically the ratio Gas Rate Drying to Feed Rate therefore is selected between 1 and 200, preferably between 10 and 150 and the Ratio Gas Rate Nozzle to Feed Rate is between 0.5 and 10, preferably between 1 and 8.

The spray drying equipment applied for the process of the present invention is a common state of the art equipment comprising a spray chamber with an atomizer and possible subsequent equipment such as e.g. a cyclone to collect a the spray dried powder and a filter unit to clean the gas from remaining particles.

The atomizer serves the purpose to finely disperse the feed solution in the form of small droplets into the spray chamber and to expose it to the hot gas.

The gas is as a rule an inert gas, typically nitrogen.

The atomizer is usually selected from a pressure drop- or a two fluid nozzle or from a rotary atomizer.

Common spray drying equipment is commercially available e.g. from Gea (Niro SD Micro), from Anhydro (SPX) or from Büchi (Büchi Mini).

The combination of the parameters determine the drying of the dispersed droplets and finally control the humidity of the spray dried product.

In a preferred embodiment a two fluid nozzle is used.

Typical further drying parameters are:

| | |
|---|---|
| Gas rate drying (kg/h) | 10 to 50, preferably 15 to 25 |
| Gas rate nozzle (kg/h) | 0.5 to 3, preferably 0.8 to 1.5 |
| Feed rate (g/min) | 3 to 18, preferably 7 to 13 |

The residual water content of the spray dried high water affinity type product can preferably be controlled in the a range of 5 w/w to 15 w/w, more preferably in the a range of 10% w/w to 15 w/w.

The bulk density of the spray dried high water affinity type product can be adjusted in the a range of 0.1 g/ml to 0.5 g/ml, preferably in the a range of 0.3 g/ml to 0.5 g/ml.

As outlined above the preferred high water affinity type products are the oligonucleotides, preferably the oligonucleotides which consist of optionally modified DNA, RNA or LNA nucleoside monomers or combinations thereof and is 10 to 40, preferably 10 to 25 nucleotides in length, which are optionally 5' amino modified and comprise GalNAc comprising cell targeting moiety as defined above.

By way of illustration the following oligonucleotides have been selected:

GN2-AM-C6-5'-caG*$^{Me}$C*G*t*a*a*a*g*a*g*a*G*G-3' (SEQ ID NO: 1)

5'-T*G*G*c*a*a*g*c*a*t*c*c*T*G*T*a-3' (SEQ ID NO: 2)

GN2-AM-C6-5'-caC*C*t*a*t*t*t*a*a*c*a*t*c*A*G*A*C-3' (SEQ ID NO: 3)

wherein AM-C6 means a C6 amino linker; * stands for phosphorothioate bridges; A,G,T and $^{Me}$C (5-methyl cytosine) are LNA nucleoside monomers and a,t,c,g are DNA nucleoside monomers and GN2 is the GalNAc cluster moiety of the formula V above (n=2; $R_2$=acetyl).

The compounds disclosed herein have the following nucleobase sequences

SEQ ID No. 1: cagcgtaaagagagg

SEQ ID No. 2: tggcaagcatcctgta

SEQ ID No. 3: cacctatttaacatcagac

EXAMPLES

Preparation of GN2-AM-C6-5'-caG*$^{Me}$C*G*t*a*a*a*g*a*g*a*G*G-3' (SEQ ID NO: 1)

The title product has been prepared in accordance with Example 3B and purified in accordance with Example 4B1 of the International Patent Publication WO 2018/215391.

Example 1

Spray Drying of GN2-AM-C6-5'-caG*$^{Me}$C*G*t*a*a*a*g*a*g*a*G*G-3' (SEQ ID NO: 1)

13 g of the title oligonucleotide were dissolved in 117 g water at room temperature. This solution was fed into a Niro SDMICRO™ (GEA Process Engineering A/S, Soeborg Denmark) through a co-current two-fluid nozzle (Ø0.5 mm, temperature 50° C., nitrogen atomizing flow rate 0.8 kg/h). The feed was atomized into a stream of hot nitrogen (Inlet temperature 220° C.) at a liquid feed rate of 10 g/min and a nitrogen flow rate of 15 kg/h. An outlet temperature of ca. 70° C. was obtained. The generated solid were separated from the gas flow by a cyclone connected to the drying chamber into a glass bottle: 11.4 g solids were collected with a residual water content of 12.3% w/w (isolated yield corrected for water content 90%) and a bulk density of 0.45 g/mL.

Examples 2 to 31

The following examples have been made in accordance with example 1, but with a variation of the key parameters.

| Example Nr. | Solid Conten % w/w | $T_{Inlet}$ ° C. | $T_{Outlet}$ ° C. | Gas rate drying kg/h | Gas rate drying/ Feed rate ratio* — | Gas rate nozzle kg/h | Gas rate nozzle/ Feed rate ratio* — | Residual Water % w/w | Yield (water corr.) % |
|---|---|---|---|---|---|---|---|---|---|
| 2 | 10 | 210 | 100 | 20 | 48 | 1.0 | 2.4 | 7.48 | 31 |
| 3 | 5 | 210 | 100 | 20 | 42 | 1.0 | 2.1 | 6.84 | 23 |
| 4 | 5 | 220 | 100 | 20 | 37 | 1.5 | 2.8 | 4.97 | 63 |
| 5 | 15 | 210 | 90 | 20 | 37 | 1.0 | 1.9 | 6.77 | 71 |
| 6 | 20 | 210 | 90 | 20 | 39 | 1.0 | 2.0 | 7.63 | 67 |
| 7 | 20 | 210 | 90 | 20 | 39 | 0.8 | 1.6 | 6.49 | 89 |
| 8 | 20 | 190 | 80 | 20 | 30 | 1.0 | 1.5 | 9.25 | 75 |
| 9 | 20 | 190 | 70 | 20 | 35 | 1.0 | 1.8 | 11.14 | 63 |
| 10 | 20 | 180 | 70 | 20 | 35 | 1.0 | 1.8 | 8.60 | 70 |
| 11 | 20 | 190 | 70 | 18 | 30 | 1.0 | 1.7 | 11.01 | 63 |
| 12 | 20 | 200 | 70 | 18 | 27 | 1.0 | 1.5 | 10.65 | 63 |
| 13 | 20 | 210 | 70 | 18 | 35 | 1.0 | 2.0 | 11.23 | 63 |
| 14 | 17.5 | 200 | 85 | 20 | 28 | 1.0 | 1.4 | 8.67 | 62 |
| 15 | 25 | 180 | 70 | 25 | 23 | 1.2 | 1.1 | 9.59 | 63 |
| 16 | 10 | 220 | 70 | 25 | 104 | 1.2 | 5.0 | 12.19 | 60 |
| 17 | 10 | 180 | 85 | 15 | 21 | 0.8 | 1.1 | 7.73 | 60 |
| 18 | 10 | 180 | 70 | 25 | 119 | 0.8 | 3.8 | 10.37 | 52 |
| 19 | 10 | 220 | 100 | 15 | 21 | 1.2 | 1.7 | 5.42 | 47 |
| 20 | 25 | 220 | 100 | 25 | 139 | 1.2 | 6.7 | 7.43 | 67 |
| 21 | 25 | 180 | 88 | 15 | 38 | 1.2 | 3.1 | 5.91 | 60 |
| 22 | 25 | 180 | 70 | 15 | 31 | 0.8 | 1.7 | 10.80 | 65 |
| 23 | 17.5 | 200 | 85 | 20 | 32 | 1.0 | 1.6 | 5.60 | 76 |
| 24 | 10 | 220 | 100 | 25 | 76 | 0.8 | 2.4 | 7.16 | 74 |
| 25 | 10 | 180 | 100 | 25 | 83 | 1.2 | 4.0 | 5.70 | 60 |
| 26 | 25 | 180 | 100 | 25 | 42 | 0.8 | 1.3 | 5.76 | 55 |
| 27 | 25 | 220 | 70 | 15 | 38 | 1.2 | 3.1 | 14.50 | 52 |
| 28 | 10 | 180 | 70 | 15 | 14 | 1.2 | 1.1 | 9.93 | 61 |
| 29 | 25 | 220 | 70 | 25 | 83 | 0.8 | 2.7 | 13.31 | 45 |
| 30 | 25 | 220 | 100 | 15 | 25 | 0.8 | 1.3 | 5.84 | 98 |
| 31 | 17.5 | 200 | 85 | 20 | 39 | 1.0 | 2.0 | 8.12 | 72 |

*The Gas rate drying/Feed rate ratio and Gas rate nozzle/Feed rate ratio are dimension-less parameters independent from the size of the drying chamber and the atomizer.

Selected Bulk Densities:

| Example Nr. | Residual Water % w/w | Bulk Density g/mL |
|---|---|---|
| 1 | 12.28 | 0.45 |
| 14 | 8.67 | 0.40 |
| 16 | 12.19 | 0.25 |
| 28 | 9.93 | 0.40 |
| 30 | 5.84 | 0.40 |
| 31 | 8.12 | 0.30 |

Comparison Example

The title product has been prepared in accordance with Example 3B, purified in accordance with Example 4B land lyophilized in accordance with Example 4B2 of the International Patent Publication WO 2018/215391.

The material obtained is very hygroscopic, electrostatically charged, not free flowing and therefore difficult to manage.

The material was therefore conditioned in a climate chamber at 21° C. and 50% rel. humidity until the weight was constant, which was achieved after 48 h.

Examples 32 to 34

Examples 32 to 34 have been performed with the following to LNA's

5'-T*G*G*c*a*a*g*c*a*t*c*c*T*G*T*a-3' (SEQ ID NO: 2) (Example 32 and 33)

GN2-AM-C6-5'-caC*C*t*a*t*t*t*a*a*c*a*t*c*A*C*A*C-3' (SEQ ID NO: 3) (Example 34)

in accordance with example 1.

| Example Nr. | Solid Content % w/w | $T_{Inlet}$ ° C. | $T_{Outlet}$ ° C. | Gas rate drying kg/h | Gas rate drying/ Feed rate | Gas rate nozzle kg/h | Gas rate nozzle/ Feed rate | Residual Water % w/w | Yield (Water corr.) % |
|---|---|---|---|---|---|---|---|---|---|
| 32 | 10 | 210 | 112 | 5 | 4 | 1.0 | 1.0 | 4.60 | 58 |
| 33 | 5 | 210 | 112 | 5 | 4 | 1.0 | 1.0 | 5.20 | 65 |
| 34 | 5 | 210 | 110 | 5 | 4 | 1.5 | 1.0 | 3.20 | 34 |

The invention claimed is:

1. A process for preparing hygroscopic oligonucleotide product with controlled residual water content, comprising spray drying an aqueous solution of the hygroscopic oligonucleotide product in a spray drying equipment, and applying spray drying parameters as follows:

| | |
|---|---|
| Oligonucleotide concentration in feed solution (% w/w) | 5 to 25 |
| Inlet $N_2$ temperature (° C.) | 180 to 220 |
| Outlet $N_2$ temperature (° C.) | 70 to 100 |
| Gas rate drying (heated $N_2$ flow rate in kg/h) | 15 to 25 |
| Gas rate nozzle ($N_2$ atomizing flow rate in kg/h) | 0.8 to 1.5 |

thereby obtaining a spray dried hygroscopic oligonucleotide product, wherein the spray drying parameters control residual water content of the spray dried ahygroscopic oligonucleotide product to a residual water content of 5% w/w to 15% w/w, wherein the hygroscopic oligonucleotide is 10 to 40 nucleotides in length, wherein the spray drying equipment comprises a spray chamber and an atomizer selected from a pressure drop-or a two fluid nozzle or from a rotary atomizer, and wherein the spray dried hygroscopic oligonucleotide product with controlled residual water content is free-flowing and easy to handle, compared to a spray dried hygroscopic oligonucleotide product without controlled residual water content.

2. The process of claim 1, wherein ratio of flow rate of heated $N_2$ to feed rate of the aqueous solution is between 1 and 200.

3. The process of claim 1, wherein ratio of flow rate of atomizing $N_2$ to feed rate of the aqueous solution is between 0.5 and 10.

4. The process of claim 1, wherein the spray drying equipment comprises a spray chamber and an atomizer selected from a two fluid nozzle.

5. The process of claim 1, wherein the spray dried hygroscopic oligonucleotide product has a bulk density of 0.1 g/ml to 0.5 g/ml.

6. The process of claim 1, wherein the hygroscopic oligonucleotide consists of optionally modified DNA, RNA or LNA nucleoside monomers or combinations thereof.

7. The process of claim 2, wherein ratio of flow rate of heated $N_2$ to feed rate of the aqueous solution is between 10 and 150.

8. The process of claim 3, wherein ratio of flow rate of atomizing $N_2$ to feed rate of the aqueous solution is between 1 and 8.

9. The process of claim 1, wherein the residual water content is 10% w/w to 15% w/w.

10. The process of claim 5, wherein the bulk density is 0.3 g/ml to 0.5 g/ml.

11. The process of claim 1, wherein the oligonucleotide is 10 to 25 nucleotides in length.

12. The process of claim 1, wherein the process avoids a water vapor conditioning procedure in a climate chamber.

* * * * *